(12) United States Patent
Lauridsen et al.

(10) Patent No.: US 8,457,280 B2
(45) Date of Patent: Jun. 4, 2013

(54) X-RAY DIFFRACTION CONTRAST TOMOGRAPHY (DCT) SYSTEM, AND X-RAY DIFFRACTION CONTRAST TOMOGRAPHY (DCT) METHOD

(71) Applicant: Danmarks Tekniske Universitet, Lyngby (DK)

(72) Inventors: Erik Mejdal Lauridsen, Harlev (DK); Henning Friis Poulsen, Roskilde (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 13/652,864

(22) Filed: Oct. 16, 2012

(65) Prior Publication Data
US 2013/0101078 A1 Apr. 25, 2013

Related U.S. Application Data

(63) Continuation of application No. 12/913,034, filed on Oct. 27, 2010.

(30) Foreign Application Priority Data

Jul. 9, 2010 (DK) .................................. 2010 70324

(51) Int. Cl.
*G01N 23/207* (2006.01)
(52) U.S. Cl.
USPC ......................................................... 378/73
(58) Field of Classification Search
USPC ............................................. 378/57, 70–90
See application file for complete search history.

(56) References Cited

U.S. PATENT DOCUMENTS

| 5,245,648 A | 9/1993 | Kinney et al. |
| 2007/0071164 A1 | 3/2007 | Shu et al. |
| 2008/0165924 A1 | 7/2008 | Wang et al. |

OTHER PUBLICATIONS

X-ray diffraction contrast tomography: a novel technique for three-dimensional grain mapping of polycrystals. Part I: direct beam case; Wolfgang Ludwig, et al.; Journal of Applied Crystallography; Jan. 16, 2008; ISSN: 0021-8898.
X-ray diffraction contrast tomography: a novel technique for three-dimensional grain mapping of polycrystals. II. The combined case; Greg Johnson, et al.; Journal of Applied Crystallography; Jan. 16, 2008; ISSN; 0021-8898.
Evaluation of imaging performance of a taper optics CCD "FreLoN" camera designed for medical imaging; Paola Coan, et al.; Journal of Synchrotron Radiation; Mar. 9, 2006; ISSN: 0909-0495.

*Primary Examiner* — Courtney Thomas
(74) *Attorney, Agent, or Firm* — Sughrue Mion, PLLC

(57) ABSTRACT

An X-ray diffraction contrast tomography system (DCT) comprising a laboratory X-ray source (2), a staging device (5) rotating a polycrystalline material sample in the direct path of the X-ray beam, a first X-ray detector (6) detecting the direct X-ray beam being transmitted through the crystalline material sample, a second X-ray detector (7) positioned between the staging device and the first X-ray detector for detecting diffracted X-ray beams, and a processing device (15) for analysing detected values. The crystallographic grain orientation of the individual grain in the polycrystalline sample is determined based on the two-dimensional position of extinction spots and the associated angular position of the sample for a set of extinction spots pertaining to the individual grain.

5 Claims, 2 Drawing Sheets

X-RAY DIFFRACTION CONTRAST TOMOGRAPHY (DCT) SYSTEM, AND X-RAY DIFFRACTION CONTRAST TOMOGRAPHY (DCT) METHOD

CROSS-REFERENCE TO RELATED APPLICATIONS

This is a continuation application of application Ser. No. 12/913,034, filed Oct. 27, 2010 which claims the benefit of priority from Danish Patent Application No. PA 2010 70324 filed on Jul. 9, 2010, all of which are incorporated herein by reference.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The present invention relates to an X-ray diffraction contrast tomography (DCT) system comprising an X-ray source for providing an X-ray beam in a direct path; a staging device for positioning and rotating a polycrystalline material sample in the direct path of the X-ray beam; a first X-ray detector located in the direct path with the staging device positioned between the first X-ray detector and the X-ray source, allowing said first X-ray detector to detect a direct X-ray beam being transmitted through the crystalline material sample; and a processing device for analysing detected values and determining crystallographic grain centre-of-mass positions and grain orientations in the polycrystalline material sample.

Such a DCT system is described in the article "X-ray diffraction contrast tomography: a novel technique for three-dimensional grain mapping of polycrystals. Part 1: direct beam case" published in Journal of Applied Crystallography (2008), 41, 319-326. A synchrotron X-ray beam is used to illuminate the sample, and the X-ray detector detects a combined absorption contrast and diffraction contrast image of the transmitted beam. By subtracting the absorption contrast part, it is possible from the remaining diffraction contrast to perform tomography of grains embedded in a polycrystalline mono-phase material. With traditional absorption or phase contrast tomography only the outer contour of a mono-phase specimen could be detected. With X-ray diffraction contrast tomography, the grains of the polycrystalline material sample under examination are imaged using the occasionally occurring diffraction contribution to the X-ray attenuation coefficient in the non-diffracted X-ray beam leaving the crystalline material sample. Each time a grain fulfils the Bragg diffraction condition a diffraction contrast occurs. The diffraction contrast appears on the detector behind the sample as an extinction spot caused by a local reduction of the transmitted beam intensity recorded on the detector. In the article, the three-dimensional grain shapes are reconstructed from a limited number of projections using algebraic reconstruction techniques (ART). The procedure for the three-dimensional grain shape reconstruction is based on spatial filtering criteria only, and the procedure can therefore be performed without analysing the grain orientations. With respect to grain orientations the article specifies that the intensity of the diffractions spots must be included in order to determine orientations, and even with integrated intensities several solutions may exist and choices have to be made. It is explained in the article that overlapping diffraction contrasts present a problem and that the sample consequently had to have only little grain orientation spread, grains of approximately the same size and tailored transverse sample dimensions in order to limit the probability of spot overlap.

Considerable efforts have been put into the development of techniques for three-dimensional grain mapping of polycrystalline materials. These techniques are utilizing X-ray beams from a synchrotron facility and employ reconstruction algorithms of the kind known in tomography in order to provide a non-destructive characterization of a sample of polycrystalline material.

Conventional X-ray absorption tomography systems as disclosed in U.S. Pat. No. 5,245,648 are able to provide a spatial representation of a sample of crystalline material. However, the contrast of such spatial representation is based on the densities of the sample and if the sample has a homogeneous density, it therefore only represents the periphery of the sample. Furthermore, if the sample comprises several phases of different materials, the internal structure within each of these phases is not visible in the representation. Moreover, the densities do not provide information of the grain structure of a crystalline material sample and hence no information about the orientation (or stress) of the grain lattice, which is equally important to determine as the spatial representation of the sample.

BRIEF SUMMARY OF THE INVENTION

The present invention aims at improving X-ray diffraction contrast tomography by making it easier to obtain the grain mapping, also from a larger sample of a mono- or multi-phase polycrystalline material.

With a view to this the X-ray diffraction contrast tomography system according to the present invention is characterized in that a second X-ray detector is positioned between the staging device and the first X-ray detector for detecting diffracted X-ray beams leaving the crystalline material sample at an angle, said second X-ray detector being adapted to allow at least a fraction of the direct X-ray beam leaving the polycrystalline material sample to continue to the first X-ray detector, and that the X-ray source is a laboratory X-ray source.

The second X-ray detector detects the diffracted X-ray beams and provides information on the crystalline structure in the grain causing the diffraction. The diffracted beam exits from the sample in an angle that is larger when the spacing between the planes in the crystal lattice is smaller. In prior art X-ray diffraction contrast tomography measurements for mapping of polycrystals, the X-ray source is a synchrotron X-ray source like the ID19 beamline of the European Synchrotron Radiation Facility in Grenoble, France. Synchrotron X-ray sources are very large facilities that are located in only a limited number of places in the world. By dispensing with such synchrotron X-ray sources and instead making the X-ray source a laboratory X-ray source the equipment used for X-ray diffraction contrast tomography becomes available for more common use, and it requires much less space. By using a laboratory X-ray source the diffraction contrast tomography becomes accessible to material science institutes in both universities and in the private sector. A laboratory X-ray source has rather small outer dimensions, such as a maximum size of less than 10 meters, and in order to enhance a compact set up the second X-ray detector detecting diffracted X-ray beams is positioned between the staging device and the first X-ray detector, and all or at least a fraction of the direct beam is allowed to pass the second X-ray detector.

In an embodiment an X-ray magnifier device is positioned in the direct path of the X-ray beam between the staging device and the first X-ray detector. The magnifier device enlarges the beam image on the first detector and allows a more detailed detection of the two-dimensional extent and position of the individual extinction spot, and thus a more precise grain shape reconstruction of the grain microstructure in the sample. The enlarged beam image also provides more detail in the absorption or phase contrast tomography information, such as presence of cracks or inclusions in the grain structure.

In a further development of this embodiment, the magnifier device magnifies the cross-sectional area of the beam onto the first X-ray detector to be at least 10 times larger than the cross-sectional area of the beam impinging on the sample. The 10 times magnification increases the resolution of the image by a factor 10 without changing the first detector. As an alternative, the resolution of the first detector could be increased but that typically involves more costs, and in some cases it is impossible, as there are intrinsic limitations on the spatial resolution of all existing x-ray detectors. It is preferred that the magnifier device magnifies the cross-sectional area of the beam onto the first X-ray detector to be at least 80 times larger than the cross-sectional area of the input beam. With a first detector having a resolution of e.g. 4 micrometer and a magnification of 80 times the resulting resolution on positions in the sample is 50 nm. Crystalline materials such as metals and ceramics that may be analysed by the above-mentioned techniques are important in processes of manufacturing for instance Solid Oxide Fuel Cells (SOFC) and microelectronics. These materials typically have grain sizes in the range of 0.5-2 micrometer and it is highly desirable to have a non-destructive and generally available characterization, allowing the internal micro structural features such as triple-phase boundaries in SOFCs and micro-cracks to be correlated to the grains structure and associated crystallographic information of a sample of crystalline material.

In an embodiment the magnifier device is a Fresnel zoneplate or a compound refractive lens located in the direct path between the second detector and the first detector. Although it is possible to locate the magnifier device between the staging device and the first detector, the preferred location between the second detector and the first detector provides the advantage that diffracted beams are completely undisturbed by the presence of the magnifier device and the second detector can be arranged at a distance from the staging device which is optimum for detection of the diffracted beams.

Preferably the first detector is positioned less than 5 meters in distance from the X-ray source as this would allow setting up the equipment in most ordinary buildings. For table top embodiments of the X-ray DCT system it is preferred that the first detector is positioned less than 2 meters in distance from the X-ray source. One advantage of a small distance is that the X-ray beam may travel through air at ambient pressure, and thus it may be possible to dispense with the traditional evacuation of the enclosure around the X-ray beam.

In an embodiment of the X-ray diffraction contrast tomography system a beam conditioning X-ray optics device is positioned in the direct path between the X-ray source and the staging device. The X-ray optics device may e.g. monochromatise the X-ray beam in order to make the X-ray beam more suitable for use in diffraction measurements where the diffraction angle depends upon the wavelength of the X-ray beam.

In an embodiment the staging device is adapted to rotate the polycrystalline material sample while the sample is exposed to the X-ray beam. The staging device can make exposures for a set of nominal rotation angles, where for each exposure the stage rotates through a predetermined angular interval around the nominal rotation angle. Alternatively, the rotation angle may remain fixed at the nominal value for each exposure.

In a situation being theoretically ideal, the second detector is positioned and sized so that it detects all of the diffracted X-ray beams, which are sufficiently intense to be above the signal-to-noise limit of the set-up. However, the X-ray diffraction contrast tomography system is capable of performing the grain mapping and reconstruction solely based on the X-ray extinction spot detected on the first detector, in particular when the sample has small dimensions in horizontal section so that grains that simultaneously cause diffraction only to a small extent overlap in the direct path of the beam. However, for larger samples having a large number of grains, such as more than 500 grains or more than 1100 grains, overlapping diffracting grains may pose problems for the reconstruction. The diffraction spots detected on the second detector can then be used to sort out which of the extinction spots detected on the first detector pertain to a particular grain. As every grain causes many extinction spots during 180° or 360° rotation of the sample it is not necessary to detect all the corresponding diffraction spots in order to perform useful sorting of the extinction spots. In an embodiment where the second X-ray detector extend along at least 40% of the area through which the diffracted X-ray beams pass, it is possible to perform such useful sorting, and the second X-ray detector may thus be located only to one side of the direct path of the X-ray beam, such as above but not below the beam. Due to symmetries in the crystal lattice structure a full set of information may be acquired when the second X-ray detector extend along at least 60% of the area through which the diffracted X-ray beams pass.

In an embodiment said second X-ray detector is adapted to allow the direct X-ray beam leaving the polycrystalline material sample to continue to the first X-ray detector by having a central hole or a central slit providing free passage of the X-ray beam in the direct path. In this manner the second X-ray detector may surround the direct path through all 360° and yet allow the X-ray beam to pass on to the first X-ray detector. It is an advantage to be able to detect on full Debye-Scherrer rings as misalignments of the staging device in relation to the direct path may then be compensated for when the detected values are analysed.

In an embodiment the second X-ray detector positioned closest to the staging device has a spatial resolution which is at least 5 times less precise than the spatial resolution of the first X-ray detector. The lower resolution of the detector positioned closest to the staging device brings the advantage of lower cost of this detector.

The present invention also relates to an X-ray diffraction contrast tomography method of determining a multi-dimensional representation of grain structures in a polycrystalline material sample, where an X-ray source provides an X-ray beam in a direct path; a staging device positions and rotates the polycrystalline material sample in the direct path of the X-ray beam; and a first X-ray detector located in the direct path detects a direct X-ray beam leaving the crystalline material sample, and a processing device analyses values received from the X-ray detector and identifies X-ray extinction spots by a reduced intensity of the detected beam, when a spot occurs, and records for each determined X-ray extinction spot the two-dimensional position of the extinction spot and the angular position of the polycrystalline sample. The values analysed in the processing device are typically images received from the X-ray detector.

In the previously mentioned article: Journal of Applied Crystallography" (2008), 41, 319-326, the grain mapping comprises two steps: sorting extinction spots according to grain of origin (known as indexing) and construction of the 3D grain morphologies (using ART). The sorting of the grains is based on using the intensity distributions of the extinction spots in order to determine grain orientations. The intensities of the diffraction spots are difficult to detect with the desired accuracy, and as already mentioned the present invention aims at improving X-ray diffraction contrast tomography by making it easier to obtain the grain mapping.

With this in view and according to the present invention, the processing device determines the crystallographic grain orientation and the centre-of-mass position of the individual grain in the polycrystalline material sample based on said two-dimensional position and said angular position for a set of extinction spots pertaining to the individual grain. By avoiding use of the intensity distribution of the extinction spots to determine the grain orientations it is no longer necessary to determine the precise values of intensities of the spots but fully sufficient to just determine the actual presence of extinction spots. This is in particular an advantage in case the direct beam is magnified before it forms the images on the first X-ray detector, because the magnification weakens the intensity of the beam and thus also weakens differences in intensities.

In a further development of the method the processing device analyses values received from a second X-ray detector detecting diffracted X-ray beams leaving the polycrystalline material sample at an angle, and based on the values received from the second X-ray detector the processing device determines at least one of the following characteristics: a) the crystal structure (position of atoms in the unit cell) of one or more individual crystalline phases present in the sample, and b) strain in grains in the polycrystalline material sample. In this modified method it is thus possible to obtain more detailed information on either information detected on the first X-ray detector for contrast tomography purposes or information detected on the first X-ray detector for diffraction purposes.

BRIEF DESCRIPTION OF THE SEVERAL VIEWS OF THE DRAWING

Illustrative examples of the invention will now be explained below with reference to the very schematic drawings, in which.

DETAILED DESCRIPTION OF THE INVENTION

In the context of the present invention a laboratory X-ray source means a compact X-ray source. The laboratory X-ray source has much smaller outer dimensions than traditional synchrotron X-ray sources, said synchrotron sources having typical diameters in the range from 30 to 1000 meters, whereas laboratory X-ray sources have typically a maximum outer dimension of 10 meters or less. Laboratory X-ray sources may be of the type having an X-ray tube, in which electrons are accelerated in a vacuum by an electric field and shot into a target piece of metal. X-rays are emitted as the electrons decelerate in the metal. The output spectrum has a continuous spectrum of X-rays with sharp peaks in intensity at certain energies depending on the kind of metal used for the target, such as copper, tungsten, silver, rhodium or molybdenum. Laboratory X-ray sources may also be of a laser type or of another available type having maximum outer dimensions of 10 meters or less, such as less than 5 meters. Laboratory X-ray sources are available from suppliers, such as Lyncean Technologies, Inc., Palo Alto, Calif., USA; Xradia Inc., Concord, Calif., USA; Proto Manufacturing Ltd., Ontario, Canada; SkyScan, Kontich, Belgium, and Phoenix X-ray, Wunstorf, Germany.

Figure 1:
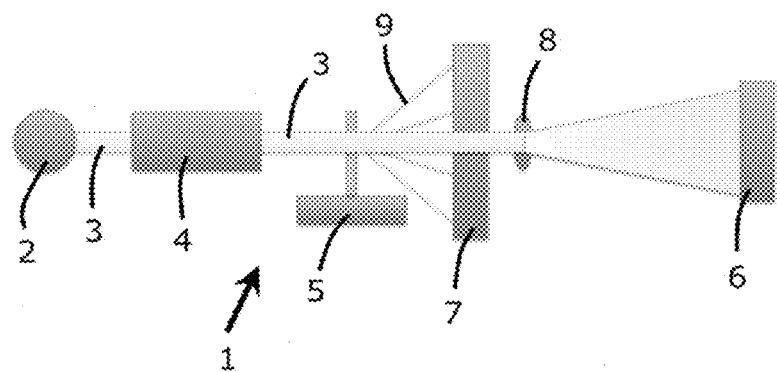
FIG. 1 illustrates an X-ray diffraction contrast tomography system according to the present invention.

FIG. 1 depicts an X-ray diffraction contrast tomography system 1. The system 1 comprises a laboratory X-ray source 2 emitting a beam of X-rays in a direct path 3. The X-ray beam passes through a beam conditioning X-ray optics device 4 which may condition the beam as required. The type of conditioning depends on the X-ray source used, and as an example the conditioning can monochromatise the beam if it has a spread in wavelengths or the conditioning may involve condenser optics, which serves to capture a larger portion of the radiation emitted from the X-ray source 2, and focussing it on the sample. Such condensing is typically useful when the X-ray source is of the type with an X-ray tube. However, the use of a beam conditioning X-ray optics device 4 may be superfluous and be dispensed with if the X-ray beam radiated by the X-ray source is sufficiently focussed and sufficiently mono-chrome.

A staging device 5 is adapted to position and rotate a crystalline material sample 10 in the direct path 3 of the X-ray beam. Such a staging device is very well-known in X-ray diffraction techniques, and it comprises a material sample or specimen holder and a stage for adjusting and rotating the material sample. The stage may be motorised and may also be translated transversely out of the direct path 3 of the beam in order to acquire reference images of the beam profile. The stage has a central, rotational axis Z and the position of the stage can be adjusted so that this rotational axis Z is perpendicular to the direct path 3 of the X-ray beam. The stage can rotate the material sample 10 about rotational axis Z either with a predefined, settable rotational speed such as in the range from 20 minutes to 5 hours per full rotation of 360° or in stepwise, incremental rotational movements that may be settable such as in the range from 0.01° to 15° per incremental rotation. For every nominal rotation angle where exposure is to occur, the stage may additionally rotate or oscillate about rotational axis Z through a predetermined angular interval around the nominal rotation angle. The stage has a default reference point for the rotational position of 0°, and preferably also a possibility for setting an actual reference point at initiation of the rotational movement of a mounted material sample. The current rotational angle w of the stage with respect to the reference point is communicated from the staging device 5 to a processing device 15. As an example, a staging device and sample holder may be obtained from the firm Bruker AXS GmbH, Karlsruhe, Germany.

Figure 2:
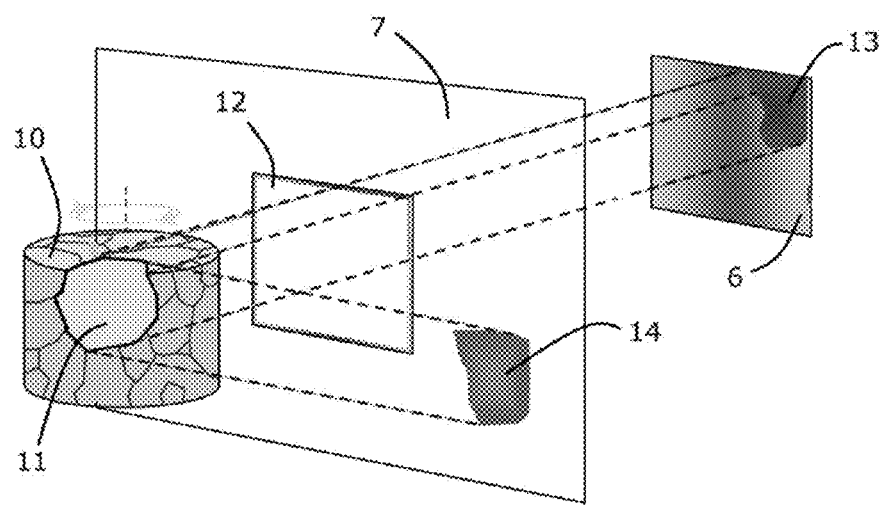
FIG. 2 illustrates a sample and a first X-ray detector and a second X-ray detector according to the invention, and FIGS. 3a-3d illustrations of a second X-ray detector detail allowing passage of at least a fraction of the direct X-ray beam.

A first X-ray detector 6 is positioned in the direct path 3 of the X-ray beam. This first detector 6 has a two-dimensional detector screen capable of detecting X-rays. The screen orientation is preferably so that the surface of the two-dimensional flat screen of the first detector is about perpendicular to the direct path 3. In the embodiment illustrated in FIG. 1 an X-ray magnifier device 8 is located between the staging device 5 and the first X-ray detector 6 so that the image on the screen of the detector is enlarged in comparison to the cross-sectional area of the X-ray beam leaving the material sample 10. In the embodiment of FIG. 2 there is no such magnifier device, and the X-ray beam leaving the material sample 10 thus arrives unmagnified to the first detector 6. As one example out of many possible, the first detector 6 may be a camera with a detector of the type charge-coupled device (CCD) or a fluorescent screen coupled to a CDD. One specific example of such a first X-ray detector is the taper optics CCD fast-readout low-noise detector developed by the European Synchrotron Radiation Facility (ESRF), cf. Journal of Synchrotron Radiation, (2006), 13, 260-270.

Figure 3A:
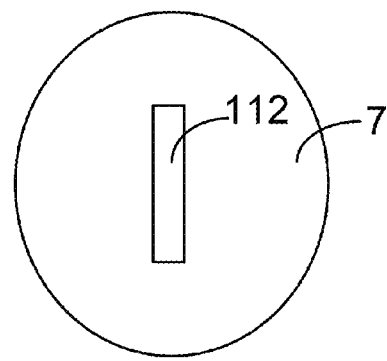
Figure 3B:
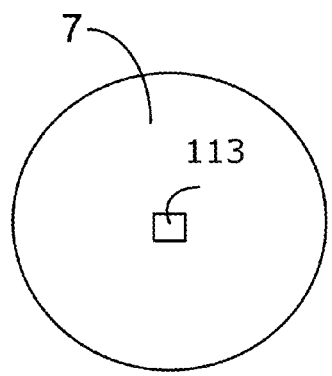
Figure 3C:
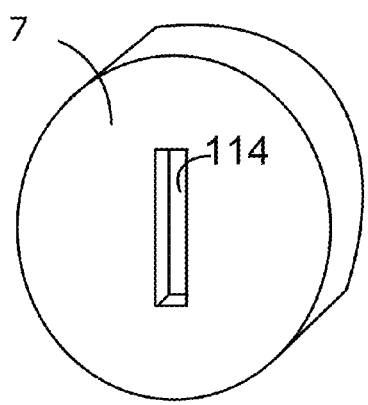
Figure 3D:
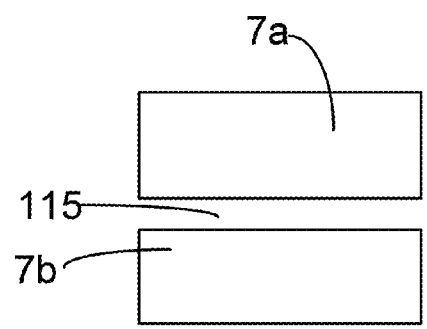

A second X-ray detector 7 is positioned between the material sample in the staging device 5 and the first X-ray detector and it has a central portion 12 in which the X-ray beam in the direct path 3 may pass unhindered through the second detector 7 and onwards to the first X-ray detector 6. The central portion 12 may be a through-going hole in the second detector 7 or it may be a hole or bore that reduces the thickness of the material in the second detector 7 to such an extent that the remaining material does not significantly attenuate the beam leaving the material sample 10. FIG. 3a depicts a partial view of the second detector 7 in the area surrounding a slit 112 passing through the material of the second detector. The slit is located in the path of the direct beam and provides free passage of the direct X-ray beam leaving the material sample so that the entire beam leaving the sample continues to the first X-ray detector 6. FIG. 3b depicts a partial view of the second detector 7 in the area surrounding a hole or aperture 113 passing through the material of the second detector. The aperture 113 is located in the path of the direct beam and provides free passage of the direct X-ray beam leaving the material sample so that the entire beam leaving the sample continues to the first X-ray detector 6. FIG. 3c depicts a partial view of the second detector 7 in the area surrounding an area of reduced thickness 114 in the material of the second detector. The area of reduced thickness is located in the path of the direct beam and provides passage of a fraction of the direct X-ray beam leaving the material sample so that said fraction of the beam leaving the sample continues to the first X-ray detector 6. The reduced thickness is preferably so thin that said fraction of the beam is at least 10%, such as in the range from 20% to 99%, and preferably at least 60%. FIG. 3d illustrates a second detector 7 made up of two parts 7a, 7b located at a distance from one another about the path of the direct X-ray beam leaving the material sample so that a free passage 115 exists between the two parts 7a, 7b through which there is free passage of the direct X-ray beam leaving the material sample.

The orientation of the second X-ray detector 7 is preferably so that the surface of the two-dimensional flat screen of the detector is about perpendicular to the direct path 3. In an alternative embodiment the second X-ray detector is a screen panel located only to one side of the direct path 3, and in a further embodiment the second X-ray detector is an arch-shaped flat screen positioned to one side of the direct beam and extending partly onto the other side of the direct beam 3, like a half-moon covering more than 180° of the circumference around the direct beam. In a further alternative embodiment the second X-ray detector is composed of two halves located at such a distance from one another that the direct beam 3 can pass unhindered in the space between the two halves.

The second X-ray detector may be of the same type as the first X-ray detector, but preferably it is of a type having less spatial resolution and larger field-of-view than the first detector. The resolution of the first X-ray detector may be in the range of 2 to 20 micro-meters, when it is of the charge-coupled device (CCD) type, or it may be of higher or lower resolution according to the desired detail of the material samples to be analysed. The resolution of the second X-ray detector 7 may be much less precise, such as from 50 to 200 micrometers. This allows for a more simple system, and the lower requirement for resolution of the second detector is possible because the second detector mainly has to detect the scattering angle of the diffraction, whereas the first X-ray detector has to determine the actual position and extent of the extinction spots with high accuracy.

The polycrystalline material sample 10 is illustrated in FIG. 2. When the staging device 5 rotates the material sample 10, or position the same in different rotational positions, and the sample is exposed to the X-ray beam in the direct path 3 then a diffraction occurs every time the lattice in a grain is oriented so with respect to the incoming beam in the direct path 3 that the Bragg diffraction condition is fulfilled.

The Bragg diffraction equation states that $2d \sin \theta = n\lambda$, where d is the interplanar distance between lattice planes in the grain, n is an integer, $\lambda$ is the wavelength of the X-ray, and $\theta$ is the scattering angle. When the beam from the X-ray source impinges the crystalline material sample positioned by the staging device 5 one or more grain of the crystalline material sample may fulfil the diffraction conditions determined by Bragg's law resulting in diffraction 9 of the X-rays impinging the grains and fulfilling the diffraction conditions.

When diffraction occurs in a crystal grain 11a part of the intensity of X-ray beam in the direct beam 3 is scattered (directed) in another direction, namely in direction of a line 9 forming the angle $2\theta$ with the direct beam 3. Due to the diffraction some of the intensity of the direct beam 3' in the area covered by the grain has been removed from the direct beam 3, and consequently an extinction spot 13 of less intensity can be detected on the first X-ray detector 6, and the position and the extension of the extinction spot in the two-dimensional area of the first detector 6 can be recorded. Due to the fact that the first X-ray detector 6 is in the line of the direct beam 3 it is consequently possible to detect the two-dimensional position of the grain in the sample 10 in this manner, but not the position in the direction of the direct beam 3. The scattered portion of the beam follows the line 9 and is detected on the second X-ray detector 7 as an illuminated diffraction spot 14.

The processing device 15 receives information in form of values for the detection of an extinction spot and the two-dimensional position of the extinction spot 13, and it associates this information with the information received from the staging device 5 on the corresponding rotational angle $\omega$ of the staging device.

Each grain is associated with a lattice, which will have numerous lattice planes that give rise to diffraction when the material sample is rotated through 90°, and for symmetry reasons even more diffractions when rotated through 180° or 360°, by the staging device 5. The number of visible diffraction events caused by a single grain may be in the range from 20 to 100. The intensity of the diffraction spots and extinction spots will vary, and it is much more demanding to detect the precise intensity than the sole fact that diffraction actually occurred.

Based on the detected information a grain reconstruction has to be performed both with respect to the three-dimensional geometrical position and extension of the individual grains and with respect to the orientation of the lattice in the individual grain. In order to do so the processing device 15 analyses the detected values and performs a sorting of the detected spots into subsets that may pertain to the same grain.

One possible manner of doing this is to sort the extinction spots 13 into groups having nearly identical vertical limits (upper and lower limits), as the vertical position of a grain remains constant while the material sample is rotated. Such a sorting will however not discern between grains positioned in an overlapping manner along the direct path 3, while producing simultaneous diffractions.

In the following there is described examples of a method of how to solve this and provide reconstructed grains orientations based on extinction spots, also in a large material sample having hundreds of grains or thousands of grains, even when the grains have large varieties in grains orientations and grain sizes.

The reconstruction of the crystalline material sample should be applicable both in case an X-ray diffraction contrast tomography system is deployed with only the first X-ray detector 6 detecting only the extinction spots 13 resulting from grains fulfilling the diffraction condition, and in the situation where an X-ray diffraction contrast tomography system is deployed with both the first X-ray detector 6 detecting extinction spots 13 and with the second X-ray detector 7 detecting X-ray diffraction spots 14. Although the method according to the present invention is made for the latter system with two X-ray detectors 6, 7 it is also applicable to the former system having only a single detector 6.

The first and second X-ray detector 6, 7 communicate with the processing device 15, such as a standard computer connected to the system 1. Besides from receiving signals representing the detected extinction spots 13 and diffraction spots 14, the processing device preferably also controls the staging device 5 so that the crystalline material sample is automatically rotated in a programmed manner during the exposure process. Preferably the processing device 15 also controls x-ray shutter(s) (not shown) required to determine the timing of the exposures of the two detectors. The shutter or shutters are placed along the beam path. The shutter is a heavily absorbing piece that may be moved in and out in front of the detector to determine when and for how long exposures are made. The one or more shutters can be placed in the beam path before or after the sample or both before and after the sample. The DCT system typically also comprises a housing or enclosure (not shown). The housing may be arranged with a possibility for evacuation of air from the area surrounding the beam path.

Due to difficulties in precisely determining the decrease in intensity of an extinction spot 13 or the intensity of a diffraction spot 14, the intensity is left out of the X-ray diffraction contrast tomography method. During one 180° rotation of the material sample there will typically be recorded many thousands of extinction spot events. For each event the geometric centre of area position of the extinction spot is determined and recorded in form of the two dimensions y, z, where y and z are the planar coordinates of the centre of area position. The centre of area position coincides in the plane with the crystallographic grain centre-of-mass position. For each event the rotational position w of the material sample is also recorded.

In a six-dimensional space where the three dimensions are the usual three-dimensional geometric space, typically denoted x, y and z, and the remaining three dimensions represent the lattice plane orientation of a grain, typically denoted by the Miller indices (hkl) for the plane orthogonal to the vector direction h, k, l. For each extinction spot the position dimensions y, z and the rotational position $\omega$ are recorded. The direction of the direct path 3 in relation to the sample 10 is also known for the specific rotational position $\omega$, so the position dimensions y, z are located on a one-dimensional line in the six-dimensional space. The extinction spot occurs at the rotational angle $\omega$ and the extinction spot represents a two-dimensional lattice plane in the grain. In the six-dimensional space the coordinates for the line and the coordinates for the plane are known for the grain. The grain producing the extinction spot is consequently located on a three-dimensional plane in the six-dimensional space.

Each individual of the many thousands of recorded extinction spot events is positioned on a three-dimensional plane in the six-dimensional space. The extinction spots pertaining to the same individual grain share the mutual condition that all the three-dimensional planes intersect in a point in the six-dimensional space. The coordinates for this point are the three-dimensional position in the geometrical space and the orientation of the lattice in the grain. Several different standard mathematical procedures exist for calculating the intersection points for three-dimensional planes in a six-dimensional space. By calculating the intersection points the extinction spots are separated in sets pertaining to individual grains, and this is done without using information on the intensity of the individual extinction spot. The method is consequently robust and easy to apply and avoids use of the intensity of the spots. The method also provides the advantage that the crystallographic grain orientation of the individual grain is obtained directly by the determination of the intersection points.

In another example of a method of how to reconstruct grain orientations based on the two-dimensional position of the extinction spots detected on the first detector 6 and the corresponding angular position $\omega$ of the material sample, there is firstly established a theoretical model of profiles and then the measured profiles are compared and paired with the theoretical profiles.

In order to establish a theoretical model the material sample is discretized into voxels having smaller volume than the average grain size of the material sample. The size of the voxels may be chosen so that in average at least ten or more voxels pertain to one and the same physical grain in the material sample. The theoretical model is then for each voxel discretized with respect to the orientation space, and for each possible orientation a theoretical profile is established. The individual profile includes information of the occurrence of extinction spots as a function of the angular positions $\omega$ of the material sample. There is consequently for each theoretical grain orientation in the crystalline material sample determined a theoretical profile comprising information of the extinction spots 13 as a function of the angular position $\omega$ of the staging device 5.

The profile data of the theoretical model are stored by the processing device 15 in a lookup table. The extinction spots 13 detected on the first X-ray detector 6 are ordered into profiles according to the geometrical location in the two-dimensional plane of the detector, corresponding to the two-dimensional position of voxels in the material sample, as a function of the angular positions $\omega$ of the material sample. The detected profiles are compared with the theoretical profiles in the lookup table and paired with the closest matching theoretical profiles. In this manner the orientation of each grain of the crystalline material sample is determined without considering the intensities of the extinction spots. The crystallographic grain orientation and the centre-of-mass position of the individual grain in the polycrystalline material sample are determined based solely on said two-dimensional position and said angular position $\omega$ for the set of extinction spots pertaining to the individual grain.

In yet another method the processing device 15 utilises values detected on the second X-ray detector 7 and representing diffraction spots 14. The diffraction spots 14 are located on Debye-Scherrer rings, the radius of which depends on d, the interplanar distance between lattice planes in the grain. The radial position of the diffraction spot as well as the actual two-dimensional position on the second detector 7 may firstly be utilised to associate particular diffraction events to certain grains, and secondly be utilised to qualify the lattice characteristics of the individual grain. For given materials there are a limited number of specific lattice forms, and the interplanar distance d between lattice planes can be used to identify the crystalline phases present in the grain, and it can further be used to identify strain in the grains, because strain in the grain changes the distance d. The additional information retrieved by using the data from the second detector may be applied to any of the above-mentioned methods.

Details from the above-mentioned embodiments and examples may be combined into other embodiments and examples within the scope of the patent claims.

The invention claimed is:

1. An X-ray diffraction contrast tomography method of determining a multi-dimensional representation of grain structures in a poly-crystalline material sample having grains, where
   an X-ray source provides an X-ray beam in a direct path,
   a staging device positions and rotates the polycrystalline material sample in the direct path of the X-ray beam,
   an X-ray detector detects diffraction spots from diffracted X-ray beams leaving the crystalline material sample,
   a processing device analyses values received from the X-ray detector and representing diffraction spots;
   wherein the processing device based on the values received from said X-ray detector determines at least one of the following characteristics: a) the crystal structure of one or more individual crystalline phases present in the sample, and b) strain in grains in the polycrystalline material sample, and
   wherein said X-ray source is a laboratory X-ray source having a target piece of metal, which X-ray source provides a continuous output spectrum of X-rays with sharp peaks in intensity at certain energies depending on the metal of the target piece.

2. An X-ray diffraction contrast tomography method according to claim 1, wherein an X-ray detector located in the direct path detects a direct X-ray beam leaving the crystalline material sample.

3. An X-ray diffraction contrast tomography method according to claim 2, wherein the processing device analyses values received from the X-ray detector located in the direct path and identifies X-ray extinction spots by a reduced intensity of the detected beam, when a spot occurs, and records for each determined X-ray extinction spot the two-dimensional position of the extinction spot and the angular position of the polycrystalline sample, wherein the processing device determines the crystallographic grain orientation and the position of the individual grain in the polycrystalline material sample based on said two-dimensional position and said angular position for a set of extinction spots pertaining to the individual grain.

4. An X-ray diffraction contrast tomography method according to claim 1, wherein the staging device rotates the polycrystalline material sample in stepwise, incremental rotational movements.

5. An X-ray diffraction contrast tomography method according to claim 4, wherein the stepwise, incremental rotational movements are settable.

\* \* \* \* \*